United States Patent [19]

Yamaguchi et al.

[11] Patent Number: 5,498,698
[45] Date of Patent: Mar. 12, 1996

[54] MEGAKARYOCYTE POTENTIATOR

[75] Inventors: Nozomi Yamaguchi, Kyoto; Masayoshi Oh-Eda; Kunihiro Hattori, both of Shizuoka, all of Japan

[73] Assignee: Chugai Seiyaku Kabushiki Kaisha, Japan

[21] Appl. No.: 256,133

[22] PCT Filed: Dec. 24, 1992

[86] PCT No.: PCT/JP92/01689

§ 371 Date: Jun. 27, 1994

§ 102(e) Date: Jun. 27, 1994

[87] PCT Pub. No.: WO93/13132

PCT Pub. Date: Jul. 8, 1994

[30] Foreign Application Priority Data

Dec. 27, 1991 [JP] Japan ..................... 3-361522
Mar. 31, 1992 [JP] Japan ..................... 4-122518

[51] Int. Cl.$^6$ .................... C07K 14/47; C07K 14/475
[52] U.S. Cl. ............................. 530/399; 530/350
[58] Field of Search ........................ 530/350, 399

[56] References Cited

FOREIGN PATENT DOCUMENTS 0517925  12/1992  European Pat. Off.

OTHER PUBLICATIONS

Kawa Kita, Medical Immunology, vol. 14, No. 4, pp. 463–470, Oct. 1987.

Ishibashi et al, Proc. Natl. Acad. Sci. USA, vol. 86, pp. 5953–5957 (Aug. 1989).

Yonemura et al, Exp. Hematol., 20:1011–1016 (1992).

Tayrien et al, The Journal of Biological Chemistry, vol. 262, No. 7, pp. 3262–3268 (Mar. 5, 1987).

Yamaguchi et al, The Journal of Biological Chemistry, vol. 269, No. 2, pp. 805–808 (Jan. 14, 1994).

*Primary Examiner*—Chhaya D. Sayala
*Attorney, Agent, or Firm*—Birch, Stewart, Kolasch & Birch

[57] ABSTRACT

A novel megakaryocyte potentiator (Meg-POT) of human origin is provided. This Meg-POT has a molecular weight of about 32,000 in SDS-PAGE. In addition, this megakaryocyte potentiator contains the following amino acid sequence in its molecule:

Gly Glu Thr Gly Gln Glu Ala Ala Pro Leu Asp Gly Val Leu. (SEQ. I.D. No. 1)

This Meg-POT is useful as a therapeutic preparation for disorders caused by decreased platelets or platelet hypofunction.

1 Claim, 3 Drawing Sheets

Fig.2

- 92.5 kd  PHOSPHORYLASE b
- 66.2    BOVINE SERUM ALBUMIN

- 45.0    OVALBUMIN

- 31.0    CARBONIC ANHYDRASE

- 21.5    SOYBEAN TRYPSIN INHIBITOR

- 14.4    LYSOZYME

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:1:

```
Gly  Glu  Thr  Gly  Gln  Glu  Ala  Ala  Pro  Leu  Asp  Gly  Val  Leu
 1              5                        10
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:2:

```
Ala  Ala  Pro  Leu  Asp  Gly  Val  Leu  Ala  Asn  Pro  Pro  Xaa  Ile  Ser  Ser
 1              5                        10                            15

Leu  Xaa  Pro  Arg  Gln  Leu  Leu  Gly  Phe  Pro
                20                        25
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO:3:

```
Gly  Glu  Thr  Gly  Gln  Glu  Ala  Ala  Pro  Leu  Asp  Gly  Val  Leu  Ala  Asn
 1              5                        10                            15
```

( 2 ) INFORMATION FOR SEQ ID NO:4:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Homo sapiens ( x i ) SEQUENCE DESCRIPTION: SEQ ID NO:4:

```
Ala  Gly  Glu  Thr  Gly  Gln  Glu  Ala  Ala  Pro  Leu  Asp  Gly  Val  Leu  Ala
1                  5                        10                       15
```

( 2 ) INFORMATION FOR SEQ ID NO:5:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Homo sapiens ( x i ) SEQUENCE DESCRIPTION: SEQ ID NO:5:

```
Leu  Ala  Gly  Glu  Xaa  Gly  Gln  Glu  Ala  Ala  Pro  Leu  Asp  Gly  Val  Leu
1                  5                        10                       15
```

MEGAKARYOCYTE POTENTIATOR

TECHNICAL FIELD

The present invention relates to a megakaryocyte potentiator (abbreviated as Meg-POT) of human origin that acts on megakaryocyte colony-Forming units (CFU-Meg) differentiated From pluripotent blood stem cells, and promotes maturation of megakaryocytes in the presence of a substance having a megakaryocyte colony-stimulating factor (abbreviated as Meg-CSF) activity, such as interleukin 3 (IL-3).

BACKGROUND ART

Platelets are one of the corporeal components of the blood having important significance with respect to hemostasis and thrombus formation in the body. Platelets are released into the blood from mature megakaryocytes formed from hematopoietic stem cells in bone marrow via megakaryocytic precursor cells and megakaryoblasts.

Factors having two different types of action are considered to be required to form megakaryocyte colonies from myeloid cells (Williams, N. et al., "J. Cell Physiol.", 110, 101 (1982)). More specifically, these factors consist of Meg-CSF, which by itself result in the formation of megakaryocyte colonies, and Meg-POT, which, although does not result in the formation of megakaryocyte colonies by itself, increases the number of megakaryocyte colonies and promotes their maturation when added together with Meg-CSF.

In human, IL-3 (Teramura, M. et al., "Exp. Hematol.", 16, 84 (1988)) and granulocyte-macrophage colony stimulating factor (Teramura, M. et al., "Exp. Hematol.", 17, 1011 (1989)) have Meg-CSF activity. In addition, examples of substances having Meg-POT activity in human include interleukin 6 (Teramura M. and Mizoguchi, H. "Int. J. Cell Cloning", 8, 245 (1990)), interleukin 11 (Teramura, M. et al., "Blood", 79, 827 (1992)), and erythropoietin (Bruno, E. et al., "Blood", 78, 671 (1989)).

However, it is also known that these substances are not specific factors for the megakaryocyte-platelet lineage, but rather also act on other blood cells as well as on cells outside the blood cell system. Thus, in the case of administration of these substances as pharmaceuticals in anticipation of their action on the megakaryocyte and platelet systems, there is also the risk of the manifestation of other actions different from that which is expected. As such, there is a need for a physiologically active substance having a high degree of usefulness as a pharmaceutical product that specifically acts on the megakaryocyte-platelet system.

DISCLOSURE OF THE INVENTION

Thus, the present invention provides a novel human megakaryocyte potentiator.

After culturing cloned cells (HPC-Y5) derived from human pancreatic cancer cells (Nozomi Yamaguchi et al., "CANCER RESEARCH", 50, 7008, (1990)) (deposited as an international deposition FERM BP-3703 under the Budapest Treaty with Fermentation Research Institute, Agency of Industrial Science and Technology on Dec. 27, (1991)), the inventors of the present invention succeeded in purifying megakaryocyte potentiator (Meg-POT) from a supernatant of that culture, and clarified the characteristics of that substance, thus leading to the completion of the present invention. Namely, the present invention provides a megakaryocyte potentiator having the following properties:

(1) dose-dependently increasing the number of megakaryocyte colonies in the presence of IL-3 in vitro;

(2) showing a single band at an approximate molecular weight of 32,000 as measured by SDS-polyacrylamide gel electrophoresis;

(3) eluting in a fraction corresponding to an acetonitrile concentration of 40–45% in 0.1% trifluoroacetic acid (TFA) in reverse phase high-performance liquid chromatography (HPLC) (column: Vydac Protein C4, 4.6× 250 mm, particle size 5 μm, Vydac); and, (4) containing the following amino acid sequence in its molecule:

Gly Glu Thr Gly Gln Glu Ala Ala Pro Leu Asp Gly Val Leu. (SEQ. I.D. No.: 1)

BRIEF DESCRIPTION OF THE DRAWINGS

FIG. 2 represents a result of molecular weight measurement by SDS-PAGE of the Meg-POT in Example 4.

BEST MODE FOR CARRYING OUT THE INVENTION

Manufacturing Method

Figure 1:
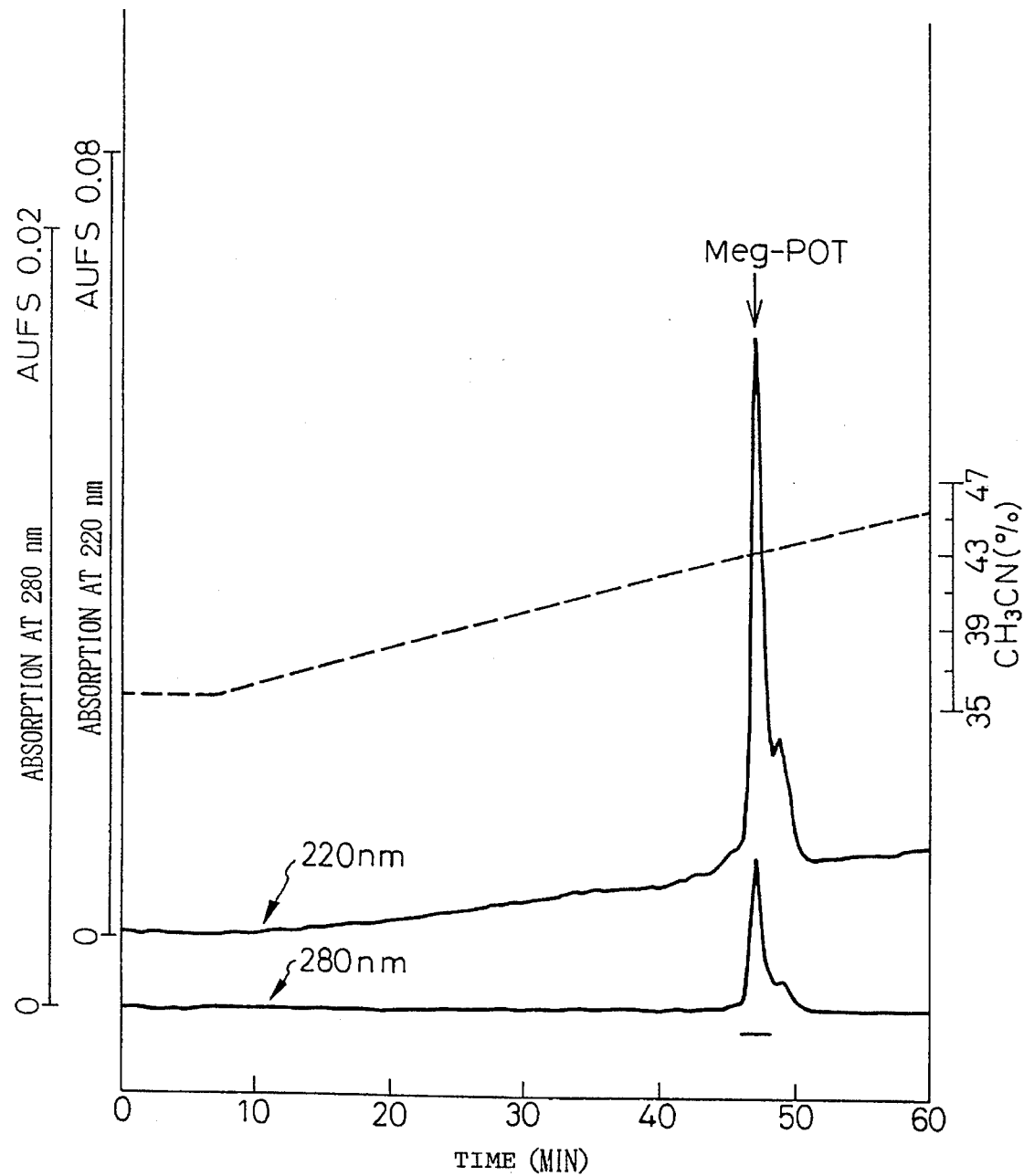
FIG. 1 represents a result of reverse phase HPLC (III) of Step 7 in Example 3.

The megakaryocyte potentiator of the present invention can be isolated and purified in the following manner from the culture supernatant of cloned cells derived from human pancreatic cancer cells (HPC-Y5). First, the cloned cells (HPC-Y5) are cultured as indicated in detail in forthcoming Example 2 followed by recovery of the culture supernatant. Next, the megakaryocyte potentiator is purified from this culture supernatant according to the procedure described in detail in Example 3.

The present megakaryocyte potentiator is purified as described in Examples. Once said megakaryocyte potentiator has been isolated or purified, and its properties have been clarified, it is clear that the present megakaryocyte potentiator can be purified using any conventional method wherein a protein is isolated and purified using properties thereof as an indication.

Moreover, the present megakaryocyte potentiator can also be prepared using genetic engineering techniques. For example, after isolating mRNA from the above-mentioned cloned cells (HPC-Y5) according to a conventional procedure, a cDNA library can be prepared based on that mRNA according to a conventional procedure. DNA probes for screening this cDNA library can be designed based on a partial amino acid sequence of the megakaryocyte potentiator clarified by the present invention. Alternatively, after determining the amino acid sequence of a particular fragment formed, by enzymatically or chemically cleaving the present megakaryocyte potentiator , DNA probes can then be designed based on the amino acid sequence of that fragment.

Next, after inserting the cDNA coding for the megakaryocyte potentiator obtained in the above manner into a suitable vector, a host is transformed with the expression vector, thereby allowing the present megakaryocyte potentiator to be prepared by culturing the transformant. Examples of hosts that can be used for this purpose include commonly used hosts, for example, procaryotic cells such as *E. coli*, lower eucaryotic cells such as yeasts, and higher eucaryotic cells such as mammalian cells.

The megakaryocyte potentiator of the present invention demonstrates the properties indicated below.

(1) Molecular Weight

The megakaryocyte potentiator of the present invention shows a single band at an approximate molecular weight of 32,000 (31,000–33,000) as measured by SDS-polyacrylamide gel electrophoresis.

(2) Partial Amino Acid Sequence

Where the megakaryocyte potentiator of the present invention, or a peptide fragment obtained by digestion of said potentiator with protease and reverse phase HPLC are subjected to Edoman degradation in a Gas-Phase Protein Sequencer Model 470A (ABI), followed by identification of the resulting PTH-amino acids in a PTH Analyzer Model 120 (ABI), said potentiator has the following amino acid sequence (SEQ ID NO: 1) in its molecule: Gly Glu Thr Gly Gln Glu Ala Ala Pro Leu Asp Gly Val Leu. As a result of correlating this sequence with the PIR protein data base and the Swiss Prot protein data base, identical sequences were not found.

(3) Megakaryocyte Potentiator Activity

The present megakaryocyte potentiator provides, megakaryocyte potentiator activity in the fractions corresponding to 40–45% acetonitrile in 0.1% TFA on reverse phase high-performance liquid chromatography (column: Vydac Protein C4, 4.6×250 mm, particle size 5 μm, Vydac).

Note, megakaryocyte potentiator activity is measured using the method described below.

Measurement of Megakaryocyte Potentiator Activity

Measurement is performed by single layer soft agar culturing using mouse bone marrow cells.

Namely, 0.2 ml of equine serum (heated for 30 minutes at 56° C., Biocell), 0.1 ml of mouse (C57BL/6N males, 6–12 weeks old) femur bone marrow cells ($2 \times 10^5$ nucleated cells), 0.2 ml of Iscove's Modified Dulbecco's medium (IMDM) containing 5 ng/ml of recombinant mouse IL-3, 0.4 ml of modified McCoy's 5A medium containing 0.75% agar, and 0.1 ml of the test sample (diluted with IMDM containing 10% equine serum) are mixed and placed in a tissue culture plastic dish having a diameter of 35 mm. After allowing to solidify, culturing is performed under conditions of a temperature of 37° C. and 100% humidity in the presence of 5% carbon dioxide gas and 95% air. On the 6th day of culturing, each agar layer is removed onto a slide glass and allowed to dry. The film-like specimens are then fixed with 5% glutaraldehyde, followed by acetylcholinesterase staining and determination of the number of megakaryocyte colonies, according to the method of Nakeff ("Pros. Soc. Exp. Biol. Med.", 151, 587, (1976)). At this time, clumps of cells containing 4 or more acetylcholinesterase positive cells are considered to be megakaryocyte colonies. The magnification of the microscope is 200X. Note, the difference between the number of megakaryocyte colonies formed where the test sample was added and the number of megakaryocyte colonies formed where recombinant IL-3 alone was added without adding the test sample (adding only IMDM containing 10% equine serum as solvent) is taken to be an indication of Meg-POT activity.

Note, since the present megakaryocyte potentiator is a glycoprotein and it is considered that corresponding deglycosylated (sugar-removed) protein has megakaryocyte potentiator activity, then the deglycosylated megakaryocyte potentiator should be included in the present invention.

The following provides a detailed explanation of the present invention through Examples. However, the present invention is not limited by these Examples.

EXAMPLE 1

Establishment of Meg-POT Producing Cells Line, HPC-Y5

A tumor obtained from the lymph node of a pancreatic cancer patient was cultured in a carbon dioxide gas incubator (carbon dioxide gas concentration 5%, humidity 100%) using RPMI1640 medium containing 10% fetal bovine serum (FBS) to establish cell line. The cloned cells were first acclimated in Ham's F10 medium containing 1% FBS, and further acclimated by gradually decreasing the FBS concentration until ultimately the cells were able to grow in Ham's F10 medium not containing any protein. The present cloned cells grew to form a single layer in a plastic dish, and the doubling time was about 33 hours (see Nozomi Yamaguchi et al., CANCER RESEARCH, 50, 7008, (1990)).

EXAMPLE 2

Subculturing of HPC-Y5 and Large Scale Culturing in Roller Bottles

The HPC-Y5 cells described in EXAMPLE 1 were subcultured in the manner indicated below. The HPC-Y5 cells were cultured in 50 ml of Ham's Nutrient Mixture F12 medium containing $10^{-8}$M sodium selenite, 100 U/ml of penicillin G potassium and 100 μg/ml of kanamycin sulfate, using a plastic culturing flask (150 cm², Corning). The culture medium was exchanged every 4 days.

For subculturing, the culture medium was removed and Dulbecco's PBS solution not containing Ca or Mg, but containing 0.125% trypsin (Gibco) and 0.01% EDTA (Wako Pure Chemical Industries) pre-incubated at 37° C., was added, followed by incubation for 5 minutes at 37° C. The cells were detached from the culturing flask by pipetting and transferred to a 15 ml-plastic centrifuge tube. The cells were then collected by centrifugation at 1500 revolutions/minute for 5 minutes. The cells were then suspended in the above-mentioned medium and distributed into 4–5 new flasks. After allowing to stand overnight, non-adhering cells and the culture medium was removed, followed by the addition of the above-mentioned medium and continuation of culturing. The culture medium was exchanged every 4 day thereafter.

In addition, large scale culturing of HPC-Y5 cells using roller bottles for use in purification of the Meg-POT described in Example 3 was performed as described below.

HPC-Y5 cells subcultured in the manner described above were collected using trypsin and EDTA in the manner above from the 150 cm² plastic culture flasks in which the HPC-Y5 cells had confluently grown. The cells were then suspended in 250 ml of the above-mentioned medium containing 0.2% fetal bovine serum (Hyclone), transferred into a 1700 cm² plastic roller bottle (Corning), and cultured at a rate of 0.5 revolutions/minute. After 7 days-culture, the culture medium was exchanged with the above-mentioned medium not containing serum, and the above-mentioned serum-free medium was exchanged every 4 day thereafter. The serum-free culture supernatant was then collected for purification.

EXAMPLE 3

Purification of Meg-POT From HPC-Y5 Cell Culture Supernatant

After adding Tween 20 at a final concentration of 0.01% to the cell culture supernatant (23.7 liters) of HPC-Y5 cells obtained according to the method described in Example 2 (27.3 liters), the supernatant was concentrated about 200 folds using PAN 1200 *Artificial Kidney* (Asahi Medica). The concentrate was dialyzed overnight at 4° C. against 10 mM acetate buffer containing 0.01% Tween 20 (pH 5.0). The internal dialysate was centrifuged (10,000×g, 60 minutes) to remove any insoluble substances, and the supernatant was used for the purification as described below.

Step 1—S-Sepharose Ion Exchange Chromatography

The above-mentioned centrifuged supernatant was loaded onto an S-Sepharose Fast Flow (Pharmacia) column (5×10 cm) equilibrated with 20 mM acetate buffer (pH 5.0) containing 0.014% Tween 20. After washing the column with the same buffer, adsorbed proteins were eluted while sequentially increasing the concentration of NaCl in the above-mentioned buffer in the order of 0.15M, 0.5M and 1.0M. As a result of measuring the activity according to the previously described method for the flow through fraction, washing fraction, and eluted fractions at each of the salt concentrations, Meg-POT activity was observed in the fraction eluted at 0.15M NaCl.

Step 2—DEAE-Sepharose Ion Exchange Chromatography

The active fraction obtained in Step 1 was dialyzed overnight at 4° C. against 10 mM Tris-HCl buffer (pH 7.4) containing 0.01% Tween 20. The internal dialysate was loaded onto a DEAE-Sepharose Fast Flow (Pharmacia) column (2.2×13 cm) equilibrated with the same buffer, followed by washing the column with same buffer. Adsorbed proteins were eluted while sequentially increasing the concentration of NaCl in the above-mentioned buffer in the order of 0.15M, 0.3M and 1.0M. As a result of measuring the activity according to the previously described method for the flow through fraction, washing fraction and eluted fractions at each of the salt concentrations, Meg-POT activity was observed in the fraction eluting at 0.15M NaCl.

Step 3—Reverse Phase HPLC (I)

After adding 5% trifluoroacetic acid (TFA) to the active fraction obtained in Step 2 to adjust ph~2, the fraction was loaded onto a reverse phase HPLC column (Vydac Protein C4, 10×250 mm, particle size 5 μm, Vydac) equilibrated with 5% acetonitrile in 0.1% TFA, at a flow rate of 1.0 ml/minute. Adsorbed proteins were eluted at a flow rate of 1 ml/minute with a linear concentration gradient of acetonitrile (5%→65%, 120 minutes, 0.5% acetonitrile/minute). Detection of the eluted proteins was performed by measuring the absorbance at 220 nm and 280 nm. Eluent was fractionated in 1 ml. As a result of measuring the activity for each of the fractions, Meg-POT activity was observed in the fraction corresponding to acetonitrile concentration of 40–45%.

Step 4—Reverse Phase HPLC (II)

After diluting the active fraction obtained in Step 3 2 folds with 0.1% TFA, the diluted fraction was loaded onto a reverse phase HPLC column (Vydac Protein C4, 4.6×250 mm, particle size 5 μm, Vydac) equilibrated with 35% acetonitrile in 0.1% TFA, at a flow rate of 10 ml/minute. Adsorbed proteins were eluted at a flow rate of 1 ml/minute with a linear concentration gradient of acetonitrile (35%→50%, 75 minutes, 0.2% acetonitrile/minute). Detection of the eluted protein was performed by measuring the absorbance at 220 nm and 280 nm. Eluent was fractionated in 1 ml. As a result of measuring the activity for each of the fractions, Meg-POT activity was observed in the fraction corresponding to acetonitrile concentration of 40–45%.

Step 5—DEAE-Ion Exchange HPLC

After lyophilizing the active fraction obtained in Step 4, the lyophilizate was dissolved in 10 mM Tris-HCl buffer (pH 8.0) containing 0.01% Tween 20, and this solution was then loaded onto a Protein Pak G-DEAE column (Waters, 8.2×75 mm), equilibrated with the same buffer as described above, at a flow rate of 0.7 ml/minute. Adsorbed proteins were eluted at a flow rate of 0.7 ml/minute with a linear concentration gradient of NaCl (0.0M→0.2M, 40 minutes, 5 mM NaCl/minute). The eluted proteins were detected at 220 nm, and eluent was fractionated in 0.7 ml. As a result of measuring the activity for each of the fractions, Meg-POT activity was observed in the fraction corresponding to an NaCl concentration of 75 mM or less.

Step 6—TSKgel G3000SW Gel Filtration

The active fraction obtained in Step 5 was then fractionated through a TSKgel G3000SW column (21.5×600 nm, guard column 21.5×75 nm, Tosoh), equilibrated with 50 mM Tris-HCl buffer (pH 7.4), containing 0.01% Tween 20 and 0.15M NaCl at a flow rate of 3 ml/minute. The proteins were detected at 220 nm. As a result of measuring the activity for each of the 3 ml fractions, Meg-POT activity was observed in the fraction having an elution time of 49–54 minutes. As such, that fraction was collected.

Step 7—Reverse Phase HPLC (III)

After adjusting ph~2 by adding 5% TFA, the active fraction obtained in Step 6 was subjected to reverse-phase HPLC under conditions identical to the reverse phase HPLC (II) of Step 4. As a result of measuring the activity for each of the fractions, Meg-POT activity was observed in the main peak (corresponding to acetonitrlle concentration of 40–45%). This result is shown in FIG. 1. The main peak indicated with the horizontal bar in FIG. 1 was collected as purified Meg-POT.

EXAMPLE 4

Molecular Weight of Megakaryocyte Potentiator (Meg-POT)

The molecular weight of the megakaryocyte potentiator purified in Example 3 was measured by sodium dodecylsulfatepolyacrylamide gel electrophoresis (SDS-PAGE). The concentration of the separation gel was 12%, and the concentration of the concentration gel was 4%. Samples were dried using a centrifugal concentrator (Tomy Seiko), dissolved in the sample buffer (pH 6.8) containing 5% 2-mercaptoethanol and 2% SDS, and boiled for 3 minutes. Electrophoresis was performed at 100 V for 30 minutes and at 140 V for 1 hour. The gel was fixed with a mixture of methanol, acetic acid and water at a ratio of 3:1:6, and protein was stained using a silver stain reagent (Daiichi Kagaku Yakuhin).

Biorad low molecular weight markers (Phosphorylase b (92.5 kd), bovine serum albumin (66.2 kd), ovalbumin (45.0 kd), carbonic anhydrase (31.0 kd), soybean trypsin inhibitor (21.5 kd) and lysozyme (14.4 kd)) were used for the molecular weight determination.

These results are indicated in FIG. 2. As is clear from FIG. 2, the megakaryocyte potentiator of the present invention (Meg-POT) demonstrated a single band at an approximate molecular weight of 32,000 (31,000–33,000).

EXAMPLE 5

Amino Acid Composition of Megakaryocyte Potentiator (Meg-POT)

The purified Meg-POT sample obtained in Example 3 was hydrolyzed in an evacuated tube with 6N HCl, containing 1% phenol for 24 hours at 110° C. Phenylisothiocyanate was added to the resulting hydrolyzate containing free amino acids and allowed to react for 25 minutes at room temperature to obtain phenylthiocarbamoyl (PTC) derivatives. The resulting PTC derivatives were quantified in a Pico-Tag amino acid analysis system (Waters). The yield of each amino acid and the amino acid composition of the Meg-POT (Ala=24 or Glx=29) are indicated in Table 1.

TABLE 1

|         | pmole  | Ala = 24 | Glx = 29 |
|---------|--------|----------|----------|
| Asx (D,N) | 542.4  | 18.2     | 18.0     |
| Glx (E,Q) | 875.2  | 29.3     | 29.0     |
| Ser (S)   | 521.1  | 17.4     | 17.3     |
| Gly (G)   | 569.9  | 19.1     | 18.9     |
| His (H)   | 38.1   | 1.3      | 1.3      |
| Arg (R)   | 602.5  | 20.2     | 20.0     |
| Thr (T)   | 223.2  | 7.5      | 7.4      |
| Ala (A)   | 717.3  | 24.0     | 23.8     |
| Pro (P)   | 589.4  | 19.7     | 19.5     |
| Tyr (Y)   | 34.5   | 1.2      | 1.1      |
| Val (V)   | 329.4  | 11.0     | 10.9     |
| Met (M)   | 35.1   | 1.2      | 1.2      |
| Cys (C)   | N.D.*  | —        | —        |
| Ile (I)   | 100.5  | 3.4      | 3.3      |
| Leu (L)   | 957.9  | 32.1     | 31.7     |
| Phe (F)   | 172.6  | 5.8      | 5.7      |
| Trp (W)   | N.D.*  | —        | —        |
| Lys (K)   | 89.6   | 3.0      | 3.0      |

*N.D.: Not determined

EXAMPLE 6

Amino Acid Sequence of Megakaryocyte Potentiator (Meg-pOT)

The purified Meg-POT sample obtained in Example 3 was subjected to Edoman degradation in a Gas-Phase protein sequencer Model 470A (Applied Biosystems Inc.). The resulting PTH-amino acids were identified in a PTH Analyzer Model 120 (Applied Biosystems Inc.). As a result, the three kinds of N-terminal amino acid sequences indicated below were observed (Sequences 1–3). In addition, the amino acid sequence of a peptide fragment, obtained by digestion of the purified Meg-POT obtained in Example 3 with $V_8$ protease and following purification by reverse-phase HPLC is shown as sequence 4. Note, Xaa indicates unidentified amino acid residue.

```
              1            5              10
Sequence 1   Leu Ala Gly Glu Xaa Gly Gln Glu Ala Ala
                         15
             Pro Leu Asp Gly Val Leu      (SEQ ID NO: 5)

1            5              10
Sequence 2   Ala Gly Glu Thr Gly Gln Glu Ala Ala Pro
                         15
             Leu Asp Gly Val Leu Ala      (SEQ ID NO: 4)

1            5              10
Sequence 3   Gly Glu Thr Gly Gln Glu Ala Ala Pro Leu Asp
                         15
             Gly Val Leu Ala Asn          (SEQ ID NO: 3)

1            5              10
Sequence 4   Ala Ala Pro Leu Asp Gly Val Leu Ala Asn Pro
                         15           20
             Pro Xaa Ile Ser Ser Leu Xaa Pro Arg Gln Leu
                         25
             Leu Gly Phe Pro              (SEQ ID NO: 2)
```

(The numbers indicated above the sequences are the cycle numbers during Edoman degradation.)

The amino acid sequence indicated below was commonly found in the amino acid sequences of Sequences 1–3 above.
Gly Glu Thr Gly Gln Glu Ala Ala Pro Leu Asp Gly Val Leu (SEQ ID NO: 1)

EXAMPLE 7

Megakaryocyte Potentiator Activity of Meg-POT

Figure 3:
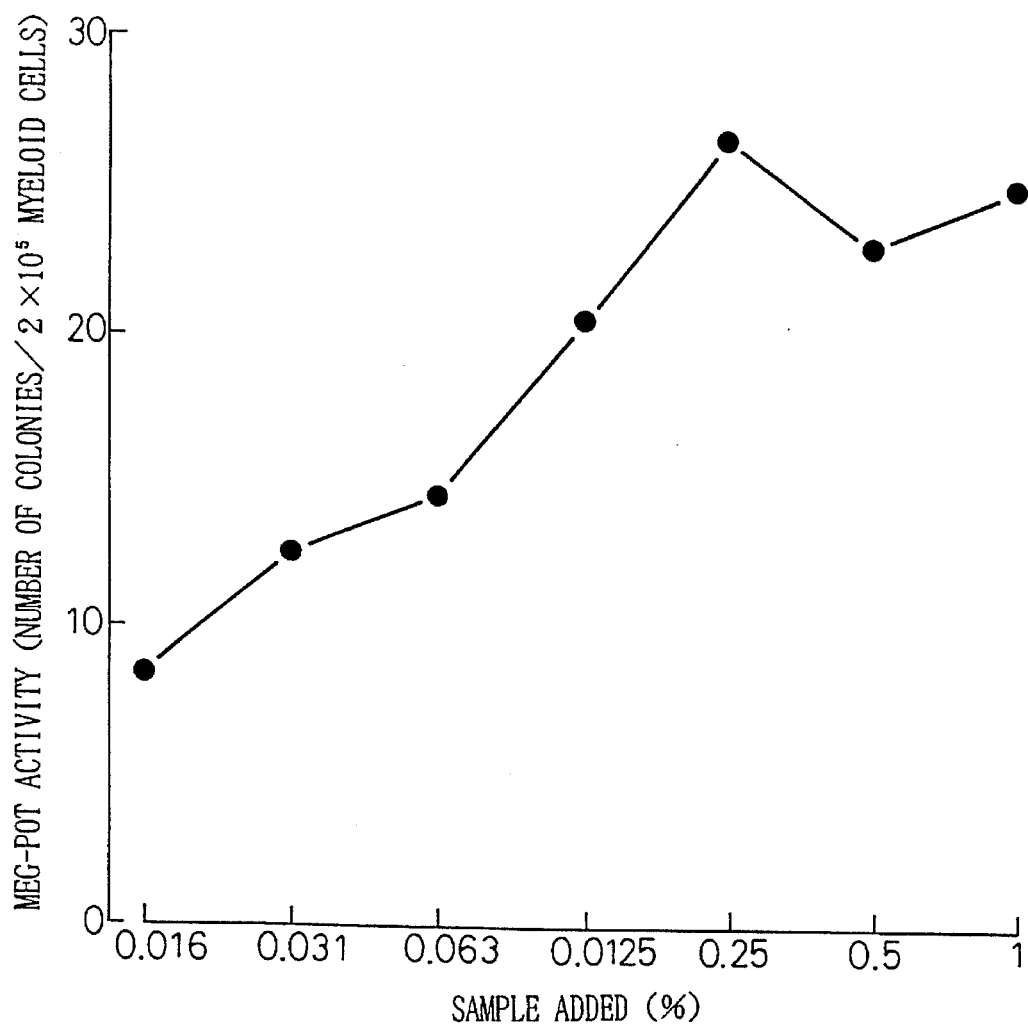
FIG. 3 represents a dose-response curve of Meg-POT activity of the megakaryocyte potentiator in Example 7. Each value is the mean of duplicate cultures. Furthermore, the Meg-POT activity on the axis of ordinate is indicated as the difference in the number of megakaryocyte colonies where the test sample was added and where the test sample was not added (recombinant mouse IL-3 alone). The number of megakaryocyte colonies where the test sample was not added were 22 and 25 colonies with an average of 23.5 colonies.

The megakaryocyte potentiator activity of Meg-POT purified in Example 3 was determined according to the method described previously using mouse bone marrow cells. Namely, the purified Meg-POT was first diluted 10-fold with IMDM containing 10% horse serum. The sample was further diluted 2, 4, 8, 16, 32 and 64 folds with the above-mentioned IMDM containing horse serum as test samples. As a result of measuring the activity of these test samples, the dose-response curve indicated in FIG. 3 was obtained.

INDUSTRIAL APPLICABILITY

Since the megakaryocyte potentiator of the present invention shows promoting activity for the growth of megakaryocyte colonies in the presence of IL-3 in vitro in a dose-dependent manner, it is expected to be useful as a therapeutic preparation for disorders accompanying, for example, decreased platelets or platelet hypofunction.

Reference to Deposited Microorganisms under Rule 13-2

Deposition Institute:

Fermentation Research Institute, Agency of Industrial Science and Technology, Ministry of International Trade and Industry Address: 1-3 Higashi 1-chome, Tsukuba-shi, Ibaraki, Japan Deposit No. and Deposition Date:

1. FERM BP-3703, Dec. 27, 1991

---

We claim:

1. A megakaryocyte potentiator having the following properties:

(1) dose-dependently increasing the number of megakaryocyte colonies in the presence of IL-3 in vitro;

(2) showing a single band at an approximate molecular weight of 32,000 as measured by SDS-polyacrylamide gel electrophoresis;

(3) eluting in a fraction corresponding to an acetonitrile concentration of 40–45% in 0.1% trifluoroacetic acid in reverse phase high-performance liquid chromatography; and, (4) containing the amino acid sequence of SEQ. I.D. No.: 1 in its molecule.

\* \* \* \* \*